United States Patent [19]

Tracy et al.

[11] Patent Number: 4,792,604

[45] Date of Patent: Dec. 20, 1988

[54] MANUFACTURE OF HALOALKYL LACTAMS

[75] Inventors: David J. Tracy, Lincoln Park; Thomas Rizzo, Bloomfield, both of N.J.

[73] Assignee: GAF Corporation, Wayne, N.J.

[21] Appl. No.: 28,362

[22] Filed: Mar. 20, 1987

[51] Int. Cl.$^4$ ............... C07D 207/263; C07D 211/76; C07D 223/10

[52] U.S. Cl. ................... 540/485; 546/243; 548/547

[58] Field of Search ............... 548/543, 547; 546/243; 540/485

[56] References Cited

U.S. PATENT DOCUMENTS 2,555,354 6/1951 Lucas et al. ................... 548/543
4,202,821 5/1980 Scheider et al. ............... 548/543

FOREIGN PATENT DOCUMENTS 1145583 3/1969 United Kingdom ............... 548/547

Primary Examiner—David B. Springer
Attorney, Agent, or Firm—Marilyn J. Maue; Joshua J. Ward

[57] ABSTRACT

A process for the manufacture of haloalkyl lactams having the formula

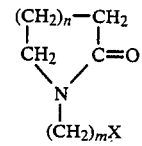

wherein n is an integer having a value of from 1 to 3; m is an integer having a value of 1 or 2 and X is chlorine or bromine in the absence of an inert solvent by reacting a hydroxyalkyl lactam of the formula

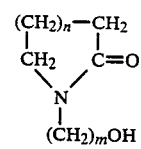

with a thionyl chloride or bromide in the liquid phase under anhydrous conditions, vaporizing and removing any excess thionyl halide along with SO$_2$ by-product from the liquid reaction mixture under vacuum followed by vacuum distillation of the remaining liquid product mixture at a temperature below its decomposition and recovering said product.

The product of this process can be obtained in greater than 90% yield and 99% purity.

13 Claims, No Drawings

MANUFACTURE OF HALOALKYL LACTAMS

In one aspect, this invention relates to an improved process for the synthesis of haloalkyl lactams and, in another aspect, to the product obtained in at least 99% purity.

The haloalkyl lactams of the present invention have diverse uses which include chemical intermediates as quaternizing agents and alkylating agents. As chemical intermediates, they are useful precursors in the synthesis of quaternized lactam products, species of which are disclosed in my co-pending patent application Ser. No. 922,923, filed Oct. 24, 1986, now U.S. Pat. No. 4,732,990 prior methods of preparing the haloalkyl lactams have been relatively time consuming and involve considerable expense, requiring the use of flammable solvents, fractional distillation using 5-10 fractionation trays, followed by tedious purification and recycle steps. Moreover, the product obtained by such prior processes has shown objectionable contamination of methylene bispyrrolidone by-product.

Accordingly, it is an object of this invention to overcome the above difficulties by an economical and commercially feasible process.

Another object of this invention is to produce N-halomethyl pyrrolidones in greater than 90% yield and at least 99% purity.

These and other objects of the invention will become apparent from the following description and disclosure.

According to this invention there is provided a process for synthesizing a N-haloalkyl lactam having the formula.

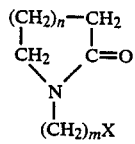

wherein
n is an integer having a value of from 1 to 3;
m is an integer having a value of from 1 to 2 and
X is chlorine or bromine
which process comprises gradually adding a hydroxyalkyl pyrrolidone having the formula

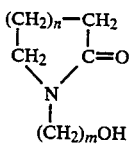

where m and n are as defined above, to at least a molar equivalent amount of $SOX_2$ wherein X is chlorine or bromine under anhydrous conditions, in the absence of an inert solvent and at a temperature sufficient to retain $SOX_2$ in the liquid state; reacting said mixture under the above conditoons; removing $SO_2$ by-product and any unreacted $SOX_2$ reactant as a vapor under vacuum at a temperature not greater than 10° above the boiling point of the $SOX_2$ compound; subjecting the remaining product solution to vacuum distillation at a higher temperature and below the product decomposition temperature oo vaporize and directly recover pure product and cooling said vaporized product to form a pure compound.

Of the above lactam reactants and lactam products, N-hydroxymethyl-2-pyrrolidone and N-halomethyl-2-pyrrolidone are preferred and N-chloromethyl-2-pyrrolidone obtained by the reaction of N-hydroxymethyl-2-pyrrolidone with thionyl chloride is most preferred.

Generally, according to the present process, the lactam reactant is added to and dissolved in thionyl halide under anhydrous conditions ataa temperature between about 0° and 40° C., preferably between about 10° and about 25° C. and the resulting mixture is reacted at about the same temperature at ambient pressure over a period of from about 1 to about 6 hours. The mole ratio of thionyl halide to lactam reactant is a critical factor in the synthesis of a product having high purity. Any excess of the hydroxyalkyl pyrrolidone promotes undesirable formation of methylene bispyrrolidone which by-product, in significant amounts, is extremely difficult to separate from the desired product. Accordingly, the mole ratio of thionyl halide to lactam reactant of betwen about 5:1 and about 1:1, preferably between about 2:1 and about 1:1, is required. Care must also be taken in maintaining the anhydrous conditions during reaction since water in the presence of thionyl halide produces hydrogen haide, which in turn, reacts with the hydroxyalkyl lactam to produce formaldehyde and lactam by-products. Accordingly, a nitrogen sparged reactor is recommended.

The present process results in product containing only minor amounts of alkylene bis lactams or oxyalkylene bis lactams. In reactions where a high excess of the thionyl halide reactant is employed, the resulting crude product mixture may also contain unreacted thionyl halide.

After the desired amount of reaction has taken place, a vacuum of between about 50 and 250 mm Hg, preferably between about 100 and about 150 mm Hg, is drawn on the reactor and the reaction mixture is heated to a temperature of between about 45° and 70° C., preferably between about 53° and about 65° C.; at which temperature and pressure, any unreacted thionyl halide, hydrogen halide and sulfur dioxide by-product is removed as a gaseous effluent. The remaining liquid reaction mixture containing product and higher boiling components is then subjected to vacuum distillation for direct recovery of product as a vaporized effluent in greater than 90% yield and purity.

The vacuum distillation is generally carried out under between about 0.05 and about 20 mm Hg, preferably between about 0.1 and about 1 mm Hg, at a temperature of from about 40° to about 100° C., preferably from about 60° to about 75° C. The vaporized product is directly recovered from the vacuum distillation zone and is cooled to room temperature. The chloromethyl pyrrolidone product crystallizes on cooling at a temperature of between about 36°-38° C. and the crystalization provides a product of high purity. For example, 100% purity is obtainable in greater than 90% yield, under the optimum conditions defined in the preferred operating parameters of the present process.

Having thus generally described the process of the present invention reference is now had to the following examples which illustrate preferred embodiments but which are not to be construed as limiting to the scope of the invention as more broadly set forth in the foreooing disclosure and in the appended claims.

EXAMPLE 1

Synthesis of N-Chloromethyl-2-Pyrrolidone

To a 1 liter round bottom flask equipped with stirrer, nitrogen inlet, condenser, and powder addition funnel was charged, 187.6 g. (1.53 moles) thionyl chloride. To the thionyl chloride, which was cooled to 10° C., 172.5 g. (1.49 moles) N-hydroxymethyl-2-pyrrolidone was added over a 2-hour period. The reaction was maintained at 10° to 25° C. during the addition and the reaction mixture was held at 25° C. for 3 hours after the addition is completed. Excess thionyl chloride together with $SO_2$ and HCl by-product were removed by heating to 60° C. at 125 mm of vacuum. The reaction flask was set for a straight take-off distillation and the remaining liquid product mixture was distilled at 0.25 to 0.4 mm Hg to remove vaporized product which boils at 66° to 70° C. The vaporized product was collected and cooled to room temperature during which the N-chloromethyl-2-pyrrolidone product, having a melting point of 36°-38° C., crystallized. The yield of 2-chloromethyl-2-pyrrolidone, 181 g., was 91% of theory.

The product was then prepared for anlysis by reacting it with methanol sodium methoxide solution and analysis for chloromethyl pyrrolidone was determined via its methyl ether derivative using gas chromatography with a 5% phenyl methyl silicone capillary column. The N-chloromethyl-2-pyrrolidone product was found to be 100% pure. The product was also analyzed for methylene bispyrrolidone. Analysis showed total absence of this by-product.

EXAMPLE 2

Synthesis of N-Bromoethyl-2-Pyrrolidone

The general procedure of Example 1 is repeated except that thionyl bromide is substituted for thionyl chloride and N-hydroxyethyl-2-pyrrolidone is substituted for N-hydroxymethyl-2-pyrrolidone. The molar ratio of thionyl compound to lactam is the same, the reaction is effected at 20° to 25° C. The vacuum distillation is carried out at 100 mm Hg pressure, thionyl bromide boiling at 80° to 85° C. The product distilled with a direct take-off at 0.1 mm Hg.

The N-bromoethyl-2-pyrrolidone product of this example is recovered in greater than 90% yield and high purity in the absence of bis-pyrrolidone contaminant.

EXAMPLE 3

Synthesis of N-Chloromethylpiperidinone

The general procedure of Example 1 is repeated except N-hydroxymethylcaprolactam is substituted for hydroxymethylpyrrolidone. A 92% distilled yield of 99% pure chloromethylpiperidinone (B.P. 119°-123° at 4 mm Hg) was obtained.

EXAMPLE 4

Synthesis of N-(β-Chloroethyl)-2-Pyrrolidone

The general procedure of Example 1 is repeated except N-(β-hydroxyethyl)-2-pyrrolidone is substituted for N-hydroxymethylpyrrolidone. A 95% yield of 99% pure distilled yield of colorless product was obtained; B.P. 119°-120° at 7 mm Hg.

EXAMPLE 5

(Comparative)

Preparation of N-Chloromethylpyrrolidone

N-hydroxymethyl-2-pyrrolidone (225 g., 1.95 mole) and toluene (400 ml) were chilled to 5° C. with stirring. Thionyl chloride (257 ml, 3.3 mole) in toluene (300 ml) was added dropwise over a period of 2 hrs. and the mixture. stirred 1 hour. The toluene solvent was then stripped at 65°-85° under house vacuum. The residue distilled at 107°-110° at 2.5-3 mm Hg yielding 151.5 g. (58.2%) of product. Analysis by gas chromatography indicated that the product contained 5% methylenebispyrrolidone.

What is claimed is:

1. In the process for synthesizing a haloalkyl lactam having the formula

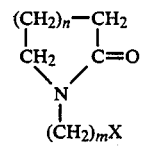

wherein
n is an integer having a value of from 1 to 3;
m is an integer having a value of 1 or 2 and
X is chlorine or bromine
by reacting a hydroxyalkyl lactam having the formula

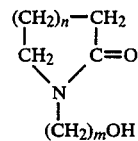

where m and n are as defined above, with at least a molar equivalent of $SOX_2$ wherein X is chlorine or bromine wherein the improvement comprises adding said hydroxyalkyl lactam to said $SOX_2$ under anhydrous conditions, in the absence of an inert solvent and at a temperature sufficient to retain $SOX_2$ in the liquid state; removing $SO_2$ by-product and any unreacted $SOX_2$ reactant under vacuum at a temperature not greater than 10° above the boiling point of the $SOX_2$ compound; subjecting the remaining product to vacuum distillation and recovering said product.

2. The process of claim 1 wherein n and m have a value of 1 and X is chlorine.

3. The process of claim 1 wherein the mole ratio of hydroxyalkyl lactam added to thionyl chloride or thionyl bromide is between about 1:5 and about 1:1.

4. The process of claim 3 wherein said mole ratio is between about 1:2 and about 1:1.

5. The process of claim 3 wherein said hydroxyalkyl lactam is gradually added to $SOX_2$ at ambient pressure.

6. The process of claim 2 wherein said hydroxyalkyl lactam is added to and reacted with $SOX_2$ at a temperature of between about 0° and 40° C.

7. The process of claim 6 wherein said reaction tmmperature is between about 10° and 25° C. and wherein the mole ratio of hydroxyalkyl lactam to $SOX_2$ is between about 1:5 and about 1:1.

8. The process of claim 7 wherein said mole ratio is between about 1:2 and about 1:1.

9. The process of claim 2 wherein $SO_2$ and hydrogen halide by-products and any unreacted $SOX_2$ are removed at a temperature of from about 45° to about 70° C. under a vacuum of between about 50 an about 250 mm Hg.

10. The process of claim 9 wherein $SO_2$ and hydrogen halide by-products and any unreacted $SOX_2$ are removed at a temperature of from about 53° to about 65° C. under a vacuum of between about 100 and about 150 mm Hg.

11. The process of claim 2 wherein said remaining product solution is vacuum distilled at a temperature of between about 40° and 100° C. under a pressure of from about 0.05 to about 20 mm Hg.

12. The process of claim 11 wherein the vacuum distillation temperature is between about 60° and 75° C. and the pressure is from about 0.1 and about 1 mm Hg.

13. The process of claim 1 wherein said product is recovered by condensation and crystallization.

* * * * *